United States Patent
Bohner et al.

(10) Patent No.: US 7,132,038 B2
(45) Date of Patent: Nov. 7, 2006

(54) METHOD AND DEVICE FOR OBTAINING 1,3 PURE BUTADIENE FROM 1,3 RAW BUTADIENE BY DISTILLATION

(75) Inventors: Gerd Bohner, Malsch (DE); Klaus Kindler, Harthausen (DE); Melanie Pahl, Mannheim (DE); Gerd Kaibel, Lampertheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 235 days.

(21) Appl. No.: 10/416,882

(22) PCT Filed: Nov. 15, 2001

(86) PCT No.: PCT/EP01/13235

§ 371 (c)(1),
(2), (4) Date: Oct. 14, 2003

(87) PCT Pub. No.: WO02/40434

PCT Pub. Date: May 23, 2002

(65) Prior Publication Data

US 2004/0045804 A1    Mar. 11, 2004

(30) Foreign Application Priority Data

Nov. 16, 2000  (DE)  ................ 100 56 841

(51) Int. Cl.
*B01D 3/42* (2006.01)
*C07C 11/167* (2006.01)

(52) U.S. Cl. .............. 203/1; 203/2; 203/98; 203/99; 203/100; 203/DIG. 19; 585/615

(58) Field of Classification Search ............... 203/1, 203/2, 100, 99, 98, DIG. 19; 196/111; 585/615, 585/800

See application file for complete search history.

(56) References Cited

U.S. PATENT DOCUMENTS

| | | | | |
|---|---|---|---|---|
| 2,471,134 A | * | 5/1949 | Wright ................. | 196/111 |
| 4,230,533 A | * | 10/1980 | Giroux ................. | 203/1 |
| 4,277,313 A | | 7/1981 | Mehra et al. | |
| 4,859,286 A | * | 8/1989 | Kaibel et al. ........... | 203/75 |
| 5,914,012 A | * | 6/1999 | Kaibel et al. ........... | 202/158 |
| 6,387,222 B1 | * | 5/2002 | Tragut et al. .......... | 203/2 |
| 6,551,465 B1 | * | 4/2003 | Van Zile et al. ....... | 202/158 |
| 6,558,515 B1 | * | 5/2003 | Steacy ................. | 203/1 |
| 6,846,389 B1 | * | 1/2005 | Kaibel et al. ........... | 203/1 |

FOREIGN PATENT DOCUMENTS

| | | |
|---|---|---|
| DE | 19 26 085 | 12/1970 |
| DE | 33 02 525 | 7/1984 |
| DE | 100 22 465 | 11/2001 |
| EP | 0 284 971 | 8/1991 |

* cited by examiner

*Primary Examiner*—Virginia Manoharan
(74) *Attorney, Agent, or Firm*—Oblon, Spivak, McClelland, Maier & Neustadt, P.C.

(57) ABSTRACT

A process for obtaining pure 1,3-butadiene from crude 1,3-butadiene by distillation is carried out in a dividing wall column in which a dividing wall is located in the longitudinal direction of the column to form an upper common column region, a lower common column region, a feed section and an offtake section.

13 Claims, 1 Drawing Sheet

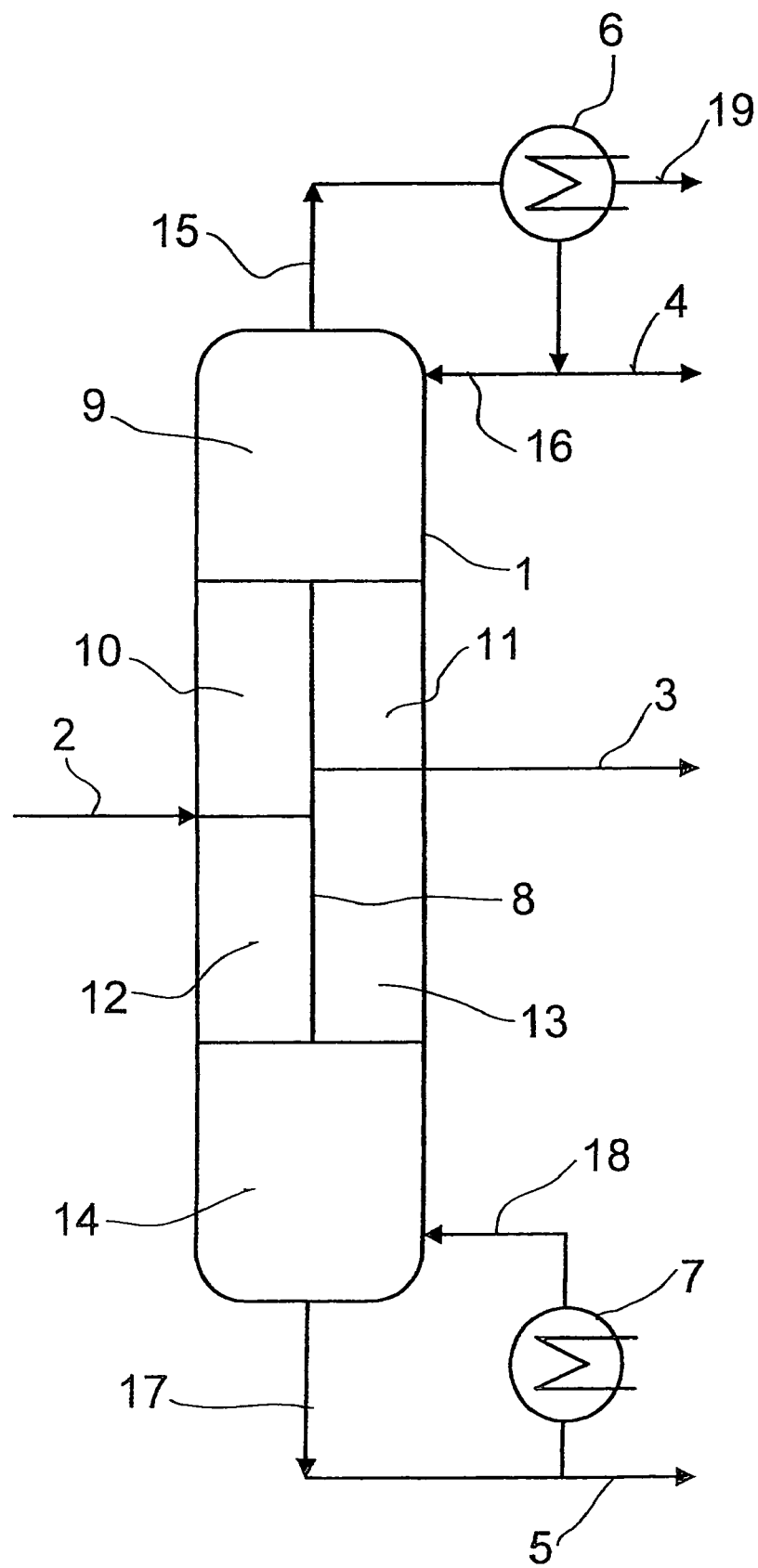

METHOD AND DEVICE FOR OBTAINING 1,3 PURE BUTADIENE FROM 1,3 RAW BUTADIENE BY DISTILLATION

BACKGROUND OF THE INVENTION

1. Field of the Invention

The present invention relates to a process for obtaining pure 1,3-butadiene from crude 1,3-butadiene by distillation and to an apparatus for carrying out this process.

2. Description of the Background

On an industrial scale, 1,3-butadiene is generally obtained from the $C_4$ fraction, i.e. from a mixture of hydrocarbons in which the $C_4$-hydrocarbons, in particular 1-butene, i-butene and 1,3-butadiene, predominate. Apart from small amounts of $C_3$- and $C_5$-hydrocarbons, the $C_4$ fraction generally comprises butynes, in particular 1-butyne (ethylacetylene) and butenyne (vinyl-acetylene). Here, a crude 1,3-butadiene, i.e. a mixture comprising from about 89 to 99.5% by weight of 1,3-butadiene, remainder impurities, is obtained initially. In order to meet specifications, this subsequently has to be purified further by distillation to give pure 1,3-butadiene. The specifications for pure 1,3-butadiene provide, in particular, for a minimum 1,3-butadiene content of 99.6% by weight and a maximum permissible propyne content of 10 ppm and 1,2-butadiene content of 20 ppm.

Owing to the low differences in the relative volatilities of the components, the isolation of crude 1,3-butadiene from the $C_4$ fraction is a complicated distillation problem and is therefore generally carried out by extractive distillation.

The acetylenic $C_4$ impurities, in particular ethylacetylene and vinylacetylene, can also be particularly advantageously converted into the desired product 1,3-butadiene by carrying out a selective hydrogenation before the extractive distillation, for example as described in U.S. Pat. No. 4,277,313, or particularly advantageously by carrying out extractive distillation and selective hydrogenation over a heterogeneous catalyst in a single column, preferably a dividing wall column, or in thermally coupled columns. Such a process is described in the German Patent Application 10022465.2, which is not a prior publication and is hereby fully incorporated by reference into the disclosure of the present invention. However, the known processes for extractive distillation or extractive distillation and selective hydrogenation, for example as described in DE 10022465.2, initially give a 1,3-butadiene which does not yet meet specifications and is therefore referred to as crude 1,3-butadiene.

According to the prior art, purification of crude 1,3-butadiene by distillation to give pure 1,3-butadiene is carried out in two stages: In a first stage, a mixture of predominantly propyne and propadiene is taken off at the top of the column at a column pressure of about 7 bar, and in a second downstream distillation column, 1,2-butadiene and $C_5$-hydrocarbons are separated off as bottom product at a pressure of about 4.5 bar. About half of the cis-2-butyne present in the crude 1,3-butadiene appears at the top of the second distillation column and about half appears at the bottom of this column. The desired product, namely pure 1,3-butadiene, is taken off at the top of the second distillation column.

EP-B 284 971 discloses thermally coupled operation of the two distillation columns. In the process of EP-B 284 971, too, the two distillation columns are operated at different pressures and thus each have to be equipped with their own vaporizer and condenser, resulting in only a slight reduction in energy consumption compared to the variant using two distillation columns which are not coupled thermally.

All known process variants for obtaining pure 1,3-butadiene from crude 1,3-butadiene by distillation started from the assumption that operation at two different pressures, with the pressure in the second distillation column being lower than that in the first distillation column, is absolutely necessary in view of the thermally sensitive dienes which tend to polymerize and also to achieve better condensability of the propyne/propadiene mixture at the top of the first distillation column.

SUMMARY OF THE INVENTION

It is an object of the present invention to provide an improved process and an apparatus for obtaining pure 1,3-butadiene from crude 1,3-butadiene by distillation, which is able to meet the required specifications in a more economical manner, in particular in respect of capital costs and energy costs.

The achievement of this object starts out from a process for obtaining pure 1,3-butadiene from crude 1,3-butadiene by distillation.

According to the present invention, the process is carried out in a dividing wall column in which a dividing wall is installed in the longitudinal direction of the column to form an upper common column region, a lower common column region, a feed section and an offtake section.

BRIEF DESCRIPTION OF THE DRAWINGS

The FIGURE shows a dividing wall distillation column by which crude 1,3-butadiene is distilled to produce pure 1,3-butadiene.

DETAILED DESCRIPTION OF THE PREFERRED EMBODIMENTS

It has surprisingly been found that the purification of crude 1,3-butadiene by distillation to give pure 1,3-butadiene can, contrary to the assumption that two-stage operation using different pressures is necessary, be carried out in a single column, namely a dividing wall column, and thus at a single pressure.

According to the present invention, the process is carried out in a dividing wall column. Dividing wall columns are distillation columns having vertical dividing walls which prevent transverse mixing of liquid and vapor streams in subregions of the column. The dividing wall, which comprises a flat metal sheet, divides the middle region of the column in the longitudinal direction into a feed section and an offtake section. The mixture to be fractionated, namely the crude 1,3-butadiene, is fed into the feed section and the product, namely the pure 1,3-butadiene, is taken off from the offtake section.

The process is generally carried out continuously.

The dividing wall column is, like, in general, any distillation column, provided with a bottom vaporizer and a condenser at the top of the column.

In the process of the present invention, the residence time in the bottom vaporizer and the associated piping system is advantageously limited to from 1 to 15 minutes, preferably from 3 to 6 minutes. This ensures trouble-free operation of the plant despite the susceptibility to polymerization of the mixture comprising numerous unsaturated components; in particular it ensures only slight fouling, if any.

In a preferred process variant, the liquid runback ratio at the upper end of the dividing wall between the feed section and offtake section of the column is regulated to a ratio of 1:1.3–2.2, preferably 1:1.6–1.9. This is preferably achieved by the liquid being collected at the upper end of the dividing wall and passed in the abovementioned ratio to the feed and offtake sections of the column by means of a regulating or setting device. This ensures a lower energy consumption.

In a further preferred process variant, the ratio of the vapor flows at the lower end of the dividing wall to the feed section and the offtake section of the column is set to a ratio of 1:0.7–1.3, preferably 1:0.95–1.1, in addition to or as an alternative to the regulation of the liquid runback ratio at the upper end of the dividing wall. The setting of the ratio of vapor flows is preferably achieved by choice of separation internals and/or by the additional installation of internals which produce a pressure drop, for example orifice plates, or by regulation of the flow of the vapor streams.

The process of the present invention is preferably carried out at a pressure at the top of the column of from 2 to 10 bar, preferably from 4 to 7 bar.

The upper common column region is preferably provided with a temperature regulator with a measurement point below the uppermost theoretical plate, preferably on the third theoretical plate from the top, which utilizes the distillate flow, the runback ratio or preferably the amount of runback as setting parameter. This ensures stable operation of the column resulting in a further improvement in the achievable product purity.

In a further process variant, a temperature regulator is provided, in addition or as an alternative, in the lower column region with a measurement point above the lowermost theoretical plate, preferably on the second theoretical plate from the bottom, which utilizes the amount taken off at the bottom as setting parameter. This additional measure achieves a further improvement in stable column operation.

Furthermore, it is possible, in addition or as an alternative, to provide level regulation at the bottom of the column, which utilizes the amount taken off at the side offtake as setting parameter.

The present invention also provides a dividing wall column for carrying out the process of the present invention for obtaining pure 1,3-butadiene from crude 1,3-butadiene by distillation.

The dividing wall column has from about 40 to 70, preferably from 50 to 60, theoretical plates.

The feedpoint for the crude 1,3-butadiene is preferably located on a theoretical plate from the 20th to the 40th, preferably from the 25th to 35th, theoretical plate.

The side offtake point for the pure 1,3-butadiene is preferably on a theoretical plate from the 25th to the 50th, preferably from the 33rd to 40th, theoretical plate.

The dividing wall is installed in the column, preferably centrally, between the 10th and the 60th, preferably between the 15th and 53rd, theoretical plates.

As regards the separation-active internals, there are in principle no restrictions; preference is given to ordered packing or trays.

In a preferred embodiment, the trays are designed, particularly in respect of the weir heights, so that the residence time in the column does not exceed 15 minutes, preferably 10 minutes.

The invention is illustrated below with the aid of a drawing and an example.

The drawing in the single FIGURE shows a dividing wall column 1 with dividing wall 8 which divides the dividing wall column 1 into a common upper column region 9, a feed section 10, 12, with enrichment section 10 and stripping section 12, an offtake section 11, 13 with stripping section 11 and an enrichment section 13 and also a common lower column region 14. The crude 1,3-butadiene 2 enters the dividing wall column 1 between the column sections 10 and 12. The pure 1,3-butadiene 3 is taken off between the column sections 11 and 13, preferably in liquid form. The vapor stream 15 obtained at the top of the column is partially condensed in the condenser 6, which may, if desired, be supplemented by an after-condenser, and is divided into the runback stream 16 and the distillate stream 4. The uncondensed fraction from the condenser 6 comprises the low-boiling impurities and is taken off in vapor form as stream 19. At the lower end of the column, the liquid 17 is partially vaporized in a vaporizer 7 and the vapor is returned to the column via the line 18. A substream 5, which comprises the high-boiling impurities, is taken off. The vaporizer 7 can be configured as a natural convection vaporizer or as a forced circulation vaporizer; in the latter case, an additional circulation pump for the liquid stream 17 is necessary. To avoid undesirable polymerization reactions, it is particularly advantageous to use a falling film evaporator in place of the forced circulation vaporizer, since such an evaporator allows the shortest residence times. To reduce the residence time of the liquid in the vaporizer system, it is useful to locate the level regulator not in the dished bottom of the column but in the line for the liquid 17.

EXAMPLE 11 027 kg/h of a crude 1,3-butadiene stream having a temperature of 43.8° C. was fed in liquid form onto the 30th theoretical plate of a dividing wall column 1 having a total of 55 theoretical plates. The crude 1,3-butadiene had the following composition:

| | |
|---|---|
| propyne | 800 ppm |
| n-butane | 9 ppm |
| i-butane | 17 ppm |
| n-butene | 28 ppm |
| i-butene | 49 ppm |
| trans-2-butene | 13 ppm |
| cis-2-butene | 0.27% by weight |
| 1,3-butadiene | 99.44% by weight |
| 1,2-butadiene | 0.14% by weight |
| 1-butine | 49 ppm |
| C4-acetylene | 82 ppm |
| C5 components | 48 ppm |
| water | 405 ppm. |

The dividing wall 8 extended from the 20th to the 51st theoretical plate. The side offtake 3 was located on the 37th theoretical plate. The column was operated at a pressure at the top of 5.5 bar and a pressure at the bottom of 5.75 bar.

Condensation at the top of the column was carried out at 40° C. 26.4 kg/h of a gaseous stream comprising low boilers was taken off from the condenser 6. From the condensed stream, a substream 4 of 4.4 kg/h was taken off. The high-boiling impurities 5 were taken off at the bottom of the column at 62° C. in an amount of 28 kg/h. At the side offtake, the desired product, namely pure 1,3-butadiene, was taken off in liquid form in an amount of 10 968.5 kg/h and at a temperature of 49.7° C. This had a 1,3-butadiene content of 99.76% by weight. The customary commercial specifications for propyne of 10 ppm and for 1,2-butadiene of 20 ppm were met. The distillation yield for 1,3-butadiene was above 99.8%.

The division ratio for the liquid at the upper end of the dividing wall 8 was 1:1.8 between feed section and the offtake section. At the lower end of the dividing wall, the vapor stream was divided between the feed section and the offtake section in a ratio of 1:1. The heating power was 4 778 kW.

The process of the present invention allowed the distillation of 90 000 metric tons per annum of crude 1,3-butadiene to be distilled to give pure 1,3-butadiene with adherence to the required specifications at a capital cost saving of 20% and an energy cost saving of 16% compared to the conventional two-stage distillation process.

We claim:

1. A process of purifying crude 1,3-butadiene, comprising:
   distilling said crude 1,3-butadiene, which enters a dividing wall column in a feed section of the column, the dividing wall positioned in the longitudinal direction of the column containing a plurality of theoretical plates separating the column into an upper common column region, a lower common column region that comprises a bottom takeoff line and a bottom vaporizer that is in communication with the lower common region by a feed line and a return line, a feed section and an offtake section; and
   withdrawing purified 1,3 butadiene at said offtake section of the column: wherein the residence time of 1,3-butadiene containing material in the bottom vaporizer and the associated feed line and return line is from 1 to 15 minutes.

2. The process as claimed in claim 1, wherein said residence time is from 3 to 6 minutes.

3. The process as claimed in claim 1, wherein liquid which forms in the column at an upper end of the dividing wall between the feed section and the offtake section of the column is regulated to a runback ratio of 1:1.3–2.2.

4. The process as claimed in claim 3, wherein said ratio is from 1:1.6–1.9.

5. The process as claimed in claim 3, wherein the upper common column region is provided with a temperature regulator with a measurement point below an uppermost theoretical plate, which utilizes flow of distillate, runback ratio or amount of runback as a setting parameter.

6. The process as claimed in claim 1, wherein the lower common column region is provided with a temperature regulator that has a measurement point above its lowermost theoretical plate, and which utilizes an amount of 1,3-butadiene containing material taken off at the bottom of the column as a setting parameter.

7. The process as claimed in claim 3, wherein the upper common column region is provided with a temperature regulator with a measurement point on a third theoretical plate from the top of the column, which utilizes an amount of runback as a setting parameter.

8. The process as claimed in claim 1, wherein vapor that forms in the column flows at a lower end of the dividing wall to the feed section and the offtake section of the column in a ratio that is set at 1:0.7–1.3.

9. The process as claimed in claim 8, wherein said ratio is 1:0.95–1.1.

10. The process as claimed in claim 1, wherein the pressure at the top of the dividing wall column ranges from 2 to 10 bar.

11. The process as claimed in claim 10, wherein said pressure ranges from 4 to 7 bar.

12. The process as claimed in claim 1, wherein the bottom of the column is provided with a level regulator which responds to the amount of 1,3-butadiene containing material that is discharged from the column at a side takeoff as a setting parameter.

13. The process as claimed in claim 1, wherein the lower common column region is provided with a temperature regulator that has a measurement point on a second theoretical plate from the bottom of the column.

* * * * *